United States Patent [19]

Kutney

[11] 4,144,237

[45] Mar. 13, 1979

[54] SYNTHETIC VINBLASTINE AND VINCRISTINE DERIVATIVES

[75] Inventor: James P. Kutney, Vancouver, Canada

[73] Assignee: The United States of America as represented by the Department of Health, Education and Welfare

[21] Appl. No.: 806,317

[22] Filed: Jun. 13, 1977

Related U.S. Application Data

[63] Continuation-in-part of Ser. No. 582,373, May 30, 1975.

[51] Int. Cl.$^2$ ........................................... C07D 519/04
[52] U.S. Cl. ................................ 260/244.4; 424/258; 465/51; 546/53; 546/50; 542/430
[58] Field of Search ..................................... 260/287 B

[56] References Cited

U.S. PATENT DOCUMENTS

4,029,663    6/1977    Gutowski et al. ............... 260/287 B

OTHER PUBLICATIONS

Rahman, Pakistan J. Sci. Ind. Res., vol. 14, No. 6 (1971), pp. 487–488.
Potier et al., J. Chem. Soc., Chem. Commun. 1975 (16), 670–671, (abstract provided 83:179350c).
Kutney et al., Chem. Abst., vol. 83, abst. 28420z (1975).
Ibid, vol. 84:59,829q (1975).
Ibid, vol. 85:160,409y, Dec. 1, 1976.

*Primary Examiner*—Nicholas S. Rizzo
*Assistant Examiner*—David E. Wheeler
*Attorney, Agent, or Firm*—John S. Roberts, Jr.

[57] ABSTRACT

Novel 3',4'-dehydro- and 4'-deoxo-vincristine and vinblastine compounds are obtained by coupling an indole unit of the catharanthine series and a dihydroindole unit of the vindoline series. Representative compounds of this series showed superior results when tested for activity against L1210 and P388 mouse leukemia.

11 Claims, No Drawings

SYNTHETIC VINBLASTINE AND VINCRISTINE DERIVATIVES

This is a continuation in part of James P. Kutney, "Synthesis of Vinblastine, Vincristine and Related Compounds," Ser. No. 582,373, filed May 30, 1975.

BACKGROUND OF THE INVENTION

The present invention relates to an improved method particularly for producing dimer alkaloid compounds especially of the Vinca alkaloid group and in particularly is an improved method for producing the antiviral, antileukemic compounds vincristine and vinblastine of Formula A.

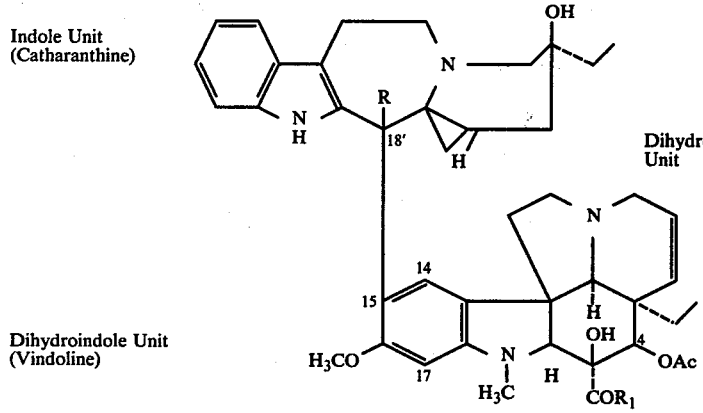

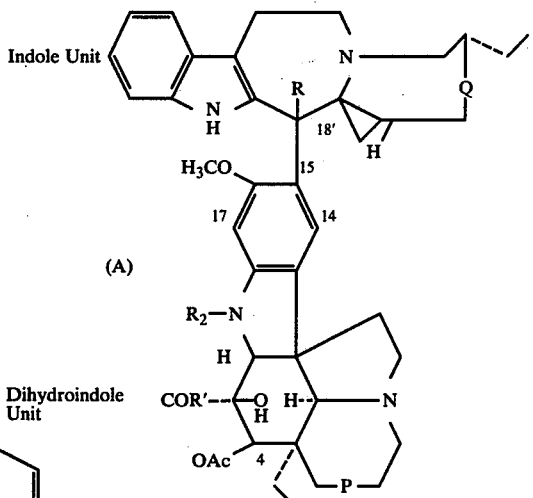

(A)

The above compound, when R is COOCH$_3$, and R$_1$ is OCH$_3$, is vinblastine (NSC 49482) and when R is COOCH$_3$, R$_1$ is OCH$_3$ and N$_1$ is N-CHO (N-formyl), vincristine (NSC 67574).

Novel 3',4'-dehydro compounds of Formula B can also be made in accordance with the method of this invention.

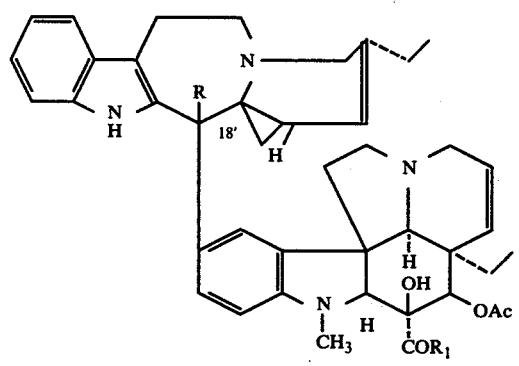

(B)

3',4'-Dehydrovinblastine N-methylamide (NSC 256954) is a compound of Formula B wherein R is COOCH$_3$ and R$_1$ is NHCH$_3$. 18'-Decarbomethoxy-3',4'-dehydrovinblastine N-methylamide (NSC 258372) is a compound of Formula B wherein R is H and R$_1$ is NHCH$_3$. Corresponding vincristine compounds are those wherein the group at N$_1$ of the vindoline unit, is N-CHO (N-formyl).

This invention further relates to novel anti-leukemic 3',4'-dehydrovinblastine and vincristine compounds of Formula B as well as 4'-deoxo compounds, which otherwise correspond to those of Formula B, but in which the 3',4'-bond is saturated.

Representative members of the novel series of compounds showed anti-leukemic activity, particularly against L1210 and P388 mouse leukemia, the novel compounds being those of the formula wherein Q is a single or double bond at the 3',4'-position of an indole unit, which, with a dihydroindole unit, constitutes a dimeric vincristine or vinblastine compound; P is a single or double bond; R is H or COO-alk and alk is alkyl of 1–6 carbon atoms; R$_1$ is O-alk, NH$_2$, NH-alk, N(alk)$_2$ or NHNH$_2$ and alkyl is of 1–6 carbon atoms; and R$_2$ is methyl or formyl.

Novel compounds of the invention include those of the above formula, more particularly those wherein:
 (a) Q is a single bond;
 (b) Q is a double bond;
 (c) R is H, including each of (a)–(b);
 (d) R is COO-alk, including each of (a)–(b);
 (e) R$_1$ is O-alk, including each of (a)–(d);
 (f) R$_1$ is NH$_2$ or NH-alk, including each of (a)–(d);
 (g) R$_2$ is CH$_3$, including each of (a)–(f);
 (h) R$_2$ is CHO, including each of (a)–(f);
 (i) P is a single bond, including each of (a)–(h); and
 (j) P is a double bond, including each of (a)–(h).

Of the novel compounds of the invention, those which are particularly preferred are:

(A) 4'-deoxovinblastine compounds, especially 4'-deoxovinblastine (NSC 250834), obtained from coupling dihydrocatharanthine and vindoline; or 4'-deoxodihydrovinblastine (NSC 256952), obtained from coupling dihydrocatharanthine and dihydrovindoline;

(B) 3',4'-dehydrovinblastine compounds, especially 3',4'-dehydrovinblastine (NSC 250833), from coupling catharanthine and vindoline; 3',4'-dehydro-18'-decarbomethoxyvinblastine, from decarbomethoxycatharanthine and vindoline; 3',4'-dehydrovinblastine amide, from catharanthine and vindoline amide; 3',4'-dehydrovinblastine N-methylamide (NSC 256954), from catharanthine and vindoline N-methylamide; 3',4'-dehydro-18'-decarbomethoxyvinblastine N-methylamide (NSC 258372), from decarbomethoxycatharanthine and vindoline N-methylamide; or 3',4'-dehydro-6,7-dihydrovinblastine (NSC 256953), from catharanthine and dihydrovindoline;

(c) 4'-deoxovincristine, from coupling of dihydrocatharanthine and N-formylvindoline; and (d) 3',4'-dehydrovincristine compounds, especially 3',4'-dehydrovincristine, from the coupling of catharanthine and N-formylvindoline; 3',4'-dehydro-18'-decarbomethoxyvincristine, from decarbomethoxycatharanthine and N-formylvindoline; 3',4'-dehydrovincristine amide, from catharanthine and N-formylvindoline amide; 3',4'-dehydrovincristine N-methylamide, from catharanthine and N-formylvindoline N-methylamide; or 3',4'-dehydro-18'-decarbomethoxyvincristine N-methylamide from decarbomethoxycatharanthine and N-formylvindoline N-methylamide.

The present series of dimeric alkaloids, including important antitumor agents, are formed from an indole, such as catharanthine, and a dihydroindole unit, e.g., vindoline, in which the halves are linked via a carbon-carbon bond involving an aliphatic center $C_{18}$ in the indole unit and an aromatic carbon $C_{15}$ in the vindoline portion. Specifically, where the catharanthine unit possesses a hydroxyl group at $C_4$, the dimer produced with vindoline will be vinblastine and also the similar catharanthine unit linked to formyl vindoline will produce vincristine.

It is further noted in the formula above that additive or substituent compounds such as amides and alkoxy compounds at $C_3$ and $C_4$ have been prepared from plant recovered vinblastine and vincristine.

In a broad sense the present method is applicable to the production of dimer products from catharanthine and dihydrocatharanthine with vindoline as starting materials and phenyl, alkyl and amide derivatives embraced by the following formulas:

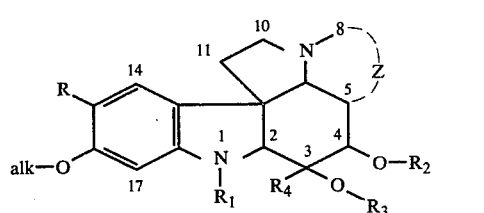

I

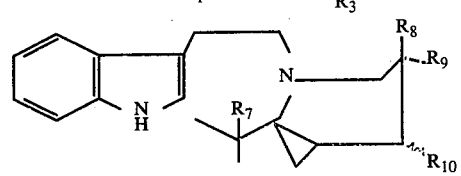

II

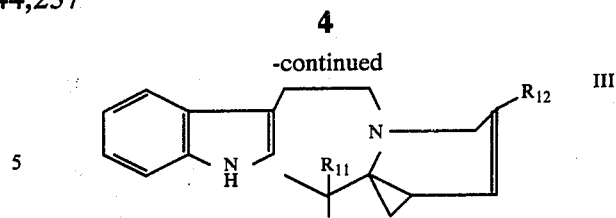

III

Formula I is as pictured and in that formula alk represents a lower alkyl group of $C_1$-$C_6$ and preferably $C_1$-$C_3$; aryl is mono-aryl such as benzyl, styryl, and xylyl; $R_1$ is a member of the group consisting of hydrogen, alk, CHO and $COR_5$ where $R_5$ is alkyl or aryl; $R_2$ and $R_3$ are members of the group consisting of hydrogen and —CO—alk: $R_4$ is a member of the group consisting of COO—alk, CONH—NH$_2$, CONH$_2$, CONHR$_6$, and CON(R$_6$)$_2$ where R is alkyl; Z is a member of the group consisting of —CH$_2$—CH$_2$— and —CH=CH— and R is a member of the indole family represented by Formula II where $R_7$ is a member of the group consisting of hydrogen, or COO—alk: $R_8$ is a member of the group consisting of hydrogen, OH, O—alk, OCO—alk or alkyl; $R_9$ is a member of the group consisting of hydrogen, OH, O—alk, OCO—alk, or alk; $R_{10}$ is a member of the group consisting of hydrogen, OH, O—alk, OCO—alk, or Formula III where $R_{11}$ is a member of the group consisting of hydrogen or COO—alk: $R_{12}$ is a member consisting of alkyl.

Compounds represented by Formula I are prepared by contacting vindoline or a vindoline derivative, when R is hydrogen, with an indole derivative represented by a compound of Formula IV where $R_{13}$ is a member of the group consisting of hydrogen or COO—alk COO—alk by a compound of Formula V where $R_{14}$ is a member of the group consisting of hydrogen or COO-alk and $R_{15}$ is a member of the group consisting of alkyl.

In Formulas I-VI and generally in this application and claims, alk and alkyl mean lower alkyl as defined in Formula I above and aryl means mono-aryl as similarly defined in Formula I.

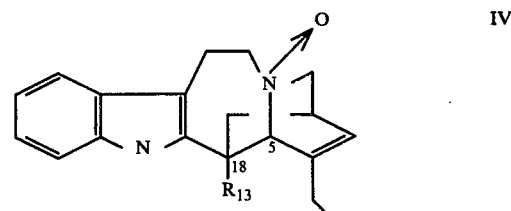

IV

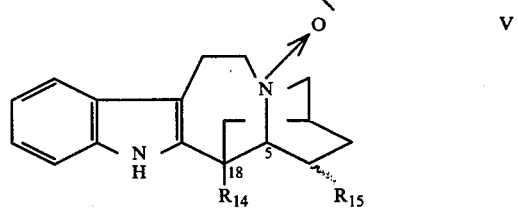

V

The so-called intermediates IV and V are not isolated during the process of the present invention and this factor is believed significantly and favorably influence the stereochemistry to produce the natural isomers at $C_{18'}$. The conditions for the complete reaction including the formation of the NO compound IV and V as well as the formation of the indoledihydroindole dimers represented by Formula I are carried out in an inert organic solvent such as preferably methylene chloride containing trifluoroacetic anhydride. As alternatives for methylene chloride useful in producing the NO compound, there may be used other polyhalo organic solvents such as carbon tetrachloride, methylene bromide, and chloroform.

As alternative reagents for the trifluoroacetic anhydride component used in fragmentation and coupling, there may be utilized trichloroacetic anhydride, acetic anhydride, acetyl chloride, and tosyl anhydride. These reagents bring about a Polonovski-type fragmentation of the $C_5$–$C_{18}$ bond in the substances shown in Formulas IV and V.

The reaction temperature, time, and pressure conditions in general are similar to those employed in the Polonovski reaction which, in its original application, involved the dealkylation of tertiary and heterocyclic amines by acylation of the corresponding N-oxides with acetic anhydride or acetyl chloride (cf. Merck Index, 8th ed., 1968, page 1203). The temperature of the fragmentation reaction may vary from $-15°$ C. to $40°$ C. and preferably from $-10°$ C. to $+10°$ C. The portions of the reaction relating to the formation of the NO compound are conducted in the open but the coupling following the fragmentation portion of the reaction is conducted under cover with inert conditions such as nitrogen or an inert gas of Group Zero of the Periodic Table such as argon, neon, helium, etc., and under a positive temperature control of about $10°$ C. to $-10°$ C. In the present combined reaction where fragmentation and coupling occur sequentially, the temperature control preferred of $10°$ to $-10°$ C. and optimally $-10°$ C. for both fragmentation and coupling, together with an inert blanket is greatly preferred.

Due to the low temperature necessary for the latter stage reaction, the reaction time may vary from several hours for several days.

PRIOR ART

U.S. Pat. No. 3,422,112 Gorman et al — Similar dimeric substances may substancesmay be produced by reacting indoles with vindoline and the coupling reaction depends upon the reactivity of the 15 position in the vindoline molecule, which is ortho to an alkoxy group. The condensation or coupling reaction is achieved under mild conditions with a Friedel-Crafts type catalyst, such as aluminum or zinc chloride in benzene. No mention is made of achieving the natural desired stereo isomers.

The present reaction differs from the above prior art in both stages, which stages are conducted in a sequential manner without isolation of an intermediate. The preparation of the intermediate NO compounds represented by Formulas IV and V is achieved at various temperatures; for example, $-77°$ C., $0°$, room temperature and above, in an inert organic solvent such as methylene chloride described above and with a peracid such as m-chloroperbenzoic acid or p-nitroperbenzoic acid. The fragmentation reaction which fragments the $C_5$–$C_{18}$ bond in the catharanthine unit is carried out in the presence of a reagent such as trifluoroacetic anhydride. The subsequent coupling reaction promotes the formation of a natural dimer bonded at $C_{18}$, (Catharanthine) and $C_{15}$ (vindoline) under an inert gas blanket preferably at a low temperature parameter control of $-10°$ C. to $+10°$ C.

As a final step in the present process, a reducing agent such as preferred alkali metal borohydride ($NaBH_4$, $KBH_4$, $LiBH_4$) is utilized which reduces the double bond on the immonium nitrogen of the catharanthine unit.

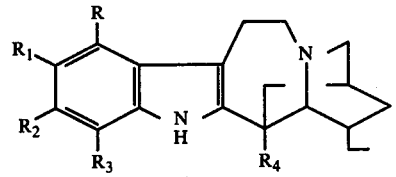

In addition to catharanthine, any indole unit represented by Formula VI may be employed. In the above Formula VI, R, $R_1$, $R_2$ and $R_3$ are members of the group consisting of hydrogen, OH, O—alk, OCOalk, alkyl or aryl. In the above Formula VI, as previously stated, alk is lower akyl $C_1$–$C_6$ and preferably $C_1$–$C_3$, and aryl is mono-aryl such as benzyl, xylyl, etc. The products of the present coupling reaction may be isolated from the reaction mixtures with standard procedures. Additionally, in some cases, due to the high complexity of the products, isolation by techniques as column, thin layer or high pressure liquid chromatography may be used.

To obtain compounds of the vincristine series, a compound of Formula B can be further oxidized to convert N—$CH_3$ at the 1-position of the vindoline unit to N—CHO. A suitable technique is oxidation with chromic acid at a low temperature as taught by U.S. Pat. No. 3,899,493, incorporated herein by reference.

THE STEREOCHEMISTRY OF THE DIMERS

The process of the present invention, as particularly applied to the reaction of catharanthine and vindoline, is technologically interesting, since the results show a successful adaptation to the product of the correct stereochemistry after coupling of $C_{18}$, on the catharanthine fraction. Thus, it is conjectured that the present process may follow that of plant enzymes involved in biosynthesis of vinblastine and vincristine.

The schematic below involves a conversion of initial electrophilic attack at the β-position of the indole ring and subsequent fragmentation between positions 5 and 18 (see Scheme 1). On the other hand, conversion of catharanthine to its N-oxide allows a Polonovski-type fragmentation and an intermediate is formed which, if not separated, prefers dimers with natural stereochemistry at $C_{18}$, as noted in XII below (see Scheme 2).

Scheme 1

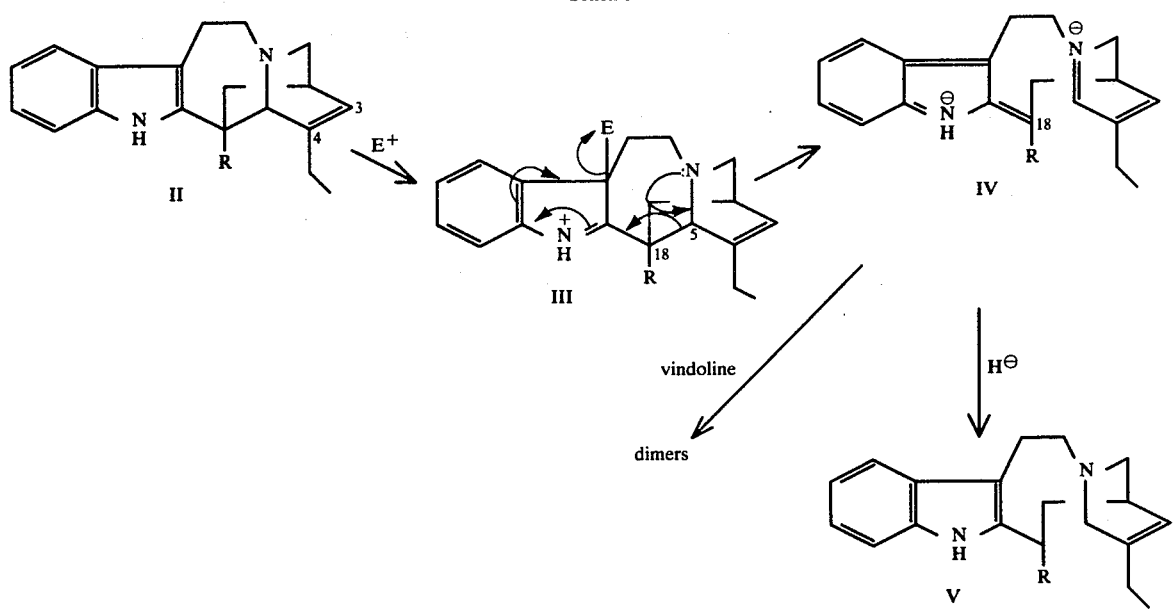

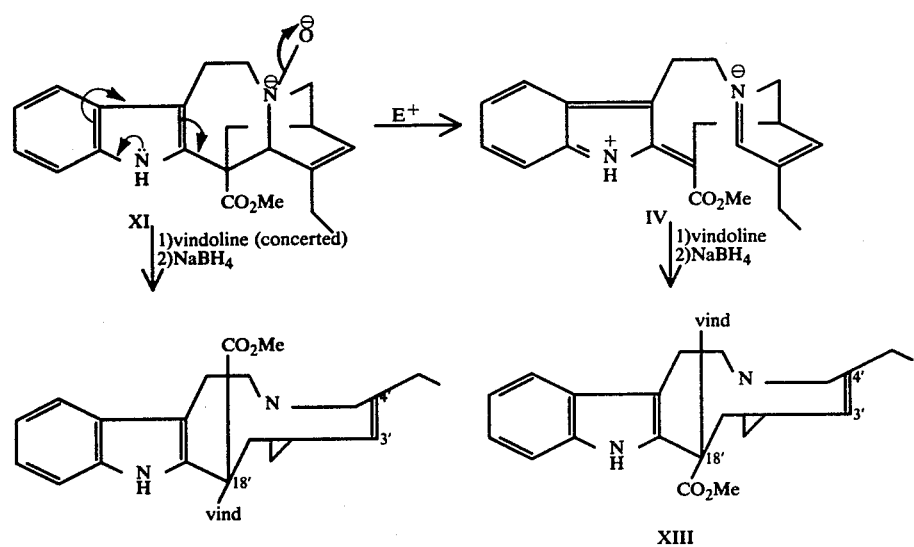

As shown in Scheme 2, if a concerted process is used wherein the intermediate is not isolated, the dimer forms in trans coplanar fashion and the resulting dimers possess natural stereochemistry at $C_{18'}$.

Tables 1 and 2 show the summary of results illustrating the preference of the preferential isolation and recovery of the preferred natural isomers XII and XV.

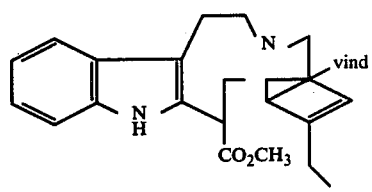

vind = vindoline
XIV

-continued

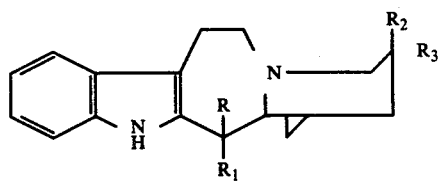

XV

TABLE 1
Coupling of Vindoline with Various N-oxides

| Expt. | N-oxide Employed [a] | Coupling Conditions [e] | Dimers Isolated (Yields) [f] | |
|---|---|---|---|---|
| 1 | catharanthine [b] | HCl, CH$_3$OH, r.t. | XIV[g] | (30) |
| 2 | catharanthine [c] | (CF$_3$CO)$_2$O, $-10°$ C. | XII | (30) |
|   |   |   | XIII | (14) |
| 3 | catharanthine [d] | (CF$_3$CO)$_2$O, $-10°$ C. | XII | (14) |
|   |   |   | XIII | (31) |
| 4 | dihydrocatharanthine [c] (11, no 3,4-double bond) | (CF$_3$CO)$_2$O, $-10°$ C. | XV, R = CO$_2$Me; R$_1$ = vind R$_2$ = CH$_2$CH$_3$; R$_3$ = H | (5) |
|   |   |   | XV, R = CO$_2$Me; R$_1$ = vind R$_2$ = H; R$_3$ = CH$_2$CH$_3$ | (13) |
|   |   |   | XV, R = vind; R$_1$ = CO$_2$Me R$_2$ = CH$_2$CH$_3$; R$_3$ = H | (14)[h] |
|   |   |   | XV, R = vind; R$_1$ = CO$_2$Me, R$_2$ = CH$_2$CH$_3$; R$_3$ = H |  |

[a] In all cases, m-chloroperbenzoic acid was employed to prepare N-oxide.
[b] Reaction was performed at room temperature and oxide purified by chromatography. During purification, N-oxide undergoes conversion to a new product, the structure of which remains undetermined at present.
[c] N-oxide prepared in situ.
[d] N-oxide isolated at low temperature.
[e] After coupling in each case the reaction mixture was treated with sodium borohydride prior to isolation of dimers.
[f] Yields quoted are not optimum. For example in related studies yields as high as 55% of XII have been obtained.
[g] Structure assignment based on spectral data only.
[h] Yield quoted on mixture of these dimers with unnatural stereochemistry at C$_{18}'$.

TABLE 2
Characterization Data for Isolated Dimers

| Dimer [a] | NMR [b,c] | MS [d] Requires | MS [d] Obtained | CD [e] | MP |
|---|---|---|---|---|---|
|  |  | C$_{46}$H$_{56}$O$_8$N$_4$ |  |  |  |
| XIV | 3.94 (s, C$_{17}$H) 2.30–3.00 (m, C$_{14}$H + aromatic) 5.72 (m, C$_{18}'$H) | 792.410 | 792.412 |  | amorphous |
| XII | 3.89 (s, C$_{17}$H) 3.54 (s, C$_{14}$H) | 792.410 | 792.405 | 227 nm(+27) | 171–173 (dec.) |
| XIII | 3.98 (s, C$_{17}$H) 3.05 (s, C$_{14}$H) | 792.410 | 792.399 | 224 nm(−31) | amorphous |
|  |  | C$_{46}$H$_{58}$O$_8$N$_4$ |  |  |  |
| XV |  | Requires | Obtained |  |  |
| R = CO$_2$Me; R$_1$ = vind; R$_2$ = CH$_2$CH$_3$; R$_3$ = H | 3.87 (s, C$_{17}$H) 3.39 (s, C$_{14}$H) | 794.425 | 794.421 | 226 nm(+17) | amorphous |
| XV R = CO$_2$Me; R$_1$ = vind; R$_2$ = H; R$_3$ = CH$_2$CH$_3$ XV[f] | 3.80 (s, C$_{17}$H) 3.42 (s, C$_{14}$H) | 794.425 | 794.422 | 227 nm(+26) | 190–194 (dec.) |
| R = vind; R$_1$ = CO$_2$Me R$_2$ = CH$_2$CH$_3$; R$_3$ = H | 4.04 (s, C$_{17}$H) 3.05 (s, C$_{14}$H) | 794.425 | 794.419 | 223 nm(−29) | amorphous |

[a] UV spectra
[b] NMR spectra taken at 100 MHz and data is given in $\tau$ values.
[c] Aromatic proton signals given for the vindoline unit.
[d] Mass spectrometer data obtained on AEI MS902.
[e] CD study used to predict chirality at C$_{18}'$ in these dimers; results presented were obtained in methanol solution.
[f] Results corroborated with an analogous method proceeding from chloroindolenine.

Relative to Experiment 4, Table 1, and dimer XV products, it is noted that two of these possess the natural stereochemistry at C$_{18}'$. It is noted that the chirality at C$_4$, the ethyl bearing center, is apparent in this synthesis of bis indole alkaloids in the vinblastine vincristine series; the other two are in isomeric series obtained and characterized previously.

EXAMPLE 1

Preparation of 3'4'-Dehydrovinblastine

In Formula I,
Z = —CH=CH—
R$_1$= CH$_3$
R$_2$50 COCH$_3$
R$_3$= H
R$_4$= COOCH$_3$
R = III where R$_{11}$ = COOCH$_3$ R$_{12}$ = CH$_2$CH$_3$ The reaction was performed under anhydrous; conditions. All glassware was oven-dried at 120° C. The solvent, methylene chloride, and coupling reagent, trifluoroacetic anhydride were distilled from P$_2$O$_5$ prior to use.

To a solution of catharanthine (201 mg, 0.60 mmol) in methylene chloride (40 ml) at $-15°$ C. was added a solution of m-chloroperbenzoic acid (111 mg, 0.65 mmol) and the solution stirred for 15 min. To the catharanthine N-oxide thus formed was added a solution of vindoline (270 mg, 0.59 mmol) in methylene chloride. The atmosphere in the reaction flask was then replaced with nitrogen and the remainder of the coupling carried out in this inert atmosphere. Trifluoroacetic anhydride (0.41 ml, 3.01 mmol) was added to the stirred solution maintained at $-15°$ C. After 22 hours this mixture was added to a solution of sodium borohydride in ethanol. After the initial vigorous evolution of gas, water and additional methylene chloride was added to the reaction mixture. The organic phase was separated and the aqueous layer washed with a second portion of methylene chloride. The organic portions were combined and washed with a solution of $K_2CO_3$. The organic phase was separated and dried with $Na_2SO_4$. The solvent was evaporated in vacuo and the residue dissolved in hot acetone. The solution was cooled and crystals of 3'4'-dehydrovinblastine were isolated. The mother liquors from the crystallization were chromatographed on silica gel plates using methanol-ethyl acetate as the eluting solvent. The combined fractions of 3'4'-dehydrovinblastine, mp 171°-173° obtained from these purifications amounted to 226 mg (0.29 mmol). Calc. for $C_{46}H_{56}O_8N_4$: 792.410. Found: 792.405.

Analysis of this product proved that it had the correct isomerism to coincide with the natural isomer.

A small amount (36.8 mg, 0.05 mmol) of the $C_{18'}$-epimer of 3'4'-dehydrovinblastine was also obtained from this reaction.

The portion of the process relating to coupling was carried out under inert conditions; i.e., with nitrogen or an inert gas of the argon family.

EXAMPLE 2

Preparation of 4'-Deoxovinblastine

In Formula I,
$Z = -CH=CH-$
$R_1 = CH_3$
$R_2 = COCH_3$
$R_3 = H$
$R_4 = COOCH_3$
$R = II$ where $R_7 = COOCH_3$ $R_8 = H$ $R_9 = 50$ $CH_2CH_3$ $R_{10} = H$ and 4'-Deoxo-4'-Epivinblastine In Formula I,
$Z = -CH=CH-$
$R_1 = CH_3$
$R_2 = COCH_3$
$R_3 = H$
$R_4 = COOCH_3$
$R = II$ where $R_7 = COOCH_3$ $R_8 = CH_2CH_3$ $R_9$ 50 H $R_{10} = H$ Dihydrocatharanthine (0.0506 gms., 0.00015 M) was dissolved in dry methylene chloride (10 ml) and the solution cooled to −15° C. with care to exclude moisture. m-Chloroperbenzoic acid (0.0293 gm, 0.00017 M) dissolved in dry methylene chloride (1 ml), was added dropwise over a period of fifteen minutes after which time the reaction mixture was checked by TLC which indicated no dihydrocatharanthine remained. Vindoline (0.0721 gms, 0.00016 M) was added directly to the reaction mixture followed by trifluoroacetic anhydride (0.1 ml, 0.0007 M) and the reaction allowed to stand at −15° C. for eighteen hours under a nitrogen atmosphere. The reaction mixture was then added to a solution of sodium borohydride (1 gm) in methanol (10 ml) and the whole stirred for fifteen minutes at 0° C. The organic solvents were removed in vacuo, the residue dissolved in water (25 ml) and the resulting solution extracted with ethyl acetate (3 × 10 ml). The combined organic phase was dried over sodium sulphate. The product obtained after removal of organic solvent was subjected to preparative TLC on silica eluting with ethyl acetate: methanol (65:35). Three bands were removed $R_f = 0.013$, 0.042, 0.031 which contained 4'-deoxovinblastine (15.7 mgms, 0.00002 M), 4'-deoxo-4'-epi vinblastine (5.7 mgms, 0.000007 M) and a mixture (13.5 mgms, 0.000017 M) of their $C_{18'}$ epimers respectively.

4'-deoxovinblastine: Calc. for $C_{46}H_{58}O_8N_4$: 794.425. Found: 794.421  4'-deoxo-4'-epivinblastine: Calc. for $C_{46}H_{58}O_8N_4$: 794.425. Found: 794.422.

EXAMPLE 3

Preparation of 18'-Decarbomethoxy-3',4'-Dehydrovinblastine

In Formula I,
$Z = -CH=CH-$
$R_1 = CH_3$
$R_2 = COCH_3$
$R_3 = H$
$R_4 = COOCH_3$
$R = III$ where $R_{11} = H$; $R_{12} = CH_2CH_3$ Decarbomethoxycatharanthine (200 mg, 0.72 mmol) was dissolved in dichloromethane (10 ml) and the solution cooled to 0° C. To this solution was added m-chloroperbenzoic acid (131 mg, 0.76 mmol) and the mixture stirred at 0° C. for 15 min., after which time thin layer chromatography indicated that N-oxide formation was complete. The mixture was cooled to −30° C. Vindoline (328 mg, 0.72 mmol) and trifluoroacetic anhydride (756 mg, 3.60 mmol) were added and the whole was stirred under a nitrogen atmosphere between −30 to −15° C. for a period of 5 hrs. The reaction mixture was treated with a solution of sodium borohydride (100 mg/10 ml) until the pH of the mixture was 8.0. After dilution with water, the mixture was extracted with dichloromethane. The organic layer was washed with sodium bicarbonate (saturated), dried over anhydrous sodium sulfate and the solvent removed in vacuo to provide a crude product (578 mg) as a brown foam. Purification of the latter by thick layer chromatography (silica gel, methanol:ethyl acetate 1:4) allowed the separation of three dimeric products.

The first product ($R_f$ 0.25, 58 mg, 11%) was the known dimer, 18'-epi-18'-decarbomethoxy-3',4'-dehydrovinblastine.

The second product ($R_f$ 0.50, 142.6 mg, 27%) was the desired dimer, 18'-decarbomethoxy-3',4'-dehydrovinblastine.

Anal.: I.R.: 3460, 3400, 2920, 1730 and 1610 cm$^{-1}$.
U.V.: 300 (3.19), 291 (3.94), 283 (3.94), 250 (4.15), 200 (4.63) nm.
CD.: 257.5 (−3.2), 224.5 (+22.6) nm.
NMR.: 8.7 (s, 1H, NH); 7.6-7.0 (m, 4H, aromatic); 6.86 (s, 1H, H-C(14)); 6.10 (s, 1H, H-C(17)); 6.0-5.8 (m, 1H, olefinic); 5.6 (d, 1H, olefinic); 5.48 (s, 1H, HCOAc); 5.25 (m, 2H, H-C(18') + olefinic); 3.95 (s, 3H, OCH$_3$); 3.80 (s, 3H, CO$_2$CH$_3$); 2.65 (s, 3H, NCH$_3$); 2.11 (s, 3H, OCOCH$_3$); 1.05 (t, 3H, CH$_2$CH$_3$); 0.6 (t, 3H, CH$_2$CH$_3$).
MS.: 83, 85, 91, 97, 121, 135 (base peak), 734.
Mol. wt.: 734.944. Calc. for $C_{44}H_{54}N_4O_6$: 734.944.
Calc. C, 72.00; H, 7.41; N, 7.33%.
Found: C, 71.52; H, 7.36; N, 6.89.

The third product ($R_f$ 0.55, 168 mg, 32%) is considered to be 19'-vindolyldecarbomethoxycatharanthine on the basis of the following data:
I.R.: 3440, 3030, 2920, 1730 and 1605 cm$^{-1}$.
U.V.: 300 (3.89), 292 (3.89), 285 (3.59), 250 (3.99), 222 (4.53) nm.
CD.: 250 (+16.3), 215 (−14.2) nm.
NMR.: 7.6-7.0 (m, 4H, aromatic); 6.62 (s, 1H, H-C(14)); 6.13 (s, 1H, H-C(17)); 6.13 (m, 1H, olefinic); 5.84

(m, 1H, olefinic); 5.41 (s, 1H, HCOAc); 5.41-4.90 (m, 3H, H-C(18') + olefinic + H-C(2)); 3.90 (s, 3H, OCH$_3$); 3.80 (s, 3H, CO$_2$CH$_3$); 3.60 (s, 1H); 2.71 (s, 3H, NCH$_3$); 2.08 (s, 3H, OCOCH$_3$); 1.12 (t, 3H, CH$_2$CH$_3$); 0.25 (t, 3H, CH$_2$CH$_3$).

MS.: 97, 121, 122, 135 (base peak), 732.
Mol. wt.: 732.926.
Calc. for C$_{44}$H$_{52}$N$_4$O$_6$: 732.928.

EXAMPLE 4

Preparation of 3', 4'-Dehydrovinblastine N-methylamide

In Formula I,
Z = —CH=CH—
R$_1$ = CH$_3$
R$_2$ = COCH$_3$
R$_3$ = H
R$_4$ = CONHCH$_3$
R = III where R$_{11}$ = COOCH$_3$; R$_{12}$ = CH$_2$CH$_3$ To a solution of catharanthine (32.4 mg, 0.1 mmol) in dichloromethane (1.7 ml) cooled to −30° C. was added a solution of m-chloroperbenzoic acid (18.2 mg, 0.105 mmol) in dichloromethane (0.6 ml) and the mixture stirred for a few minutes. A solution of vindoline N-methylamide (45.5 mg, 0.1 mmol) in dichloromethane (1 ml) and trifluoroacetic anhydride (81 μl, 0.5 mmol) were added and the whole mixture was stirred under a nitrogen atmosphere at −30° C. for 5 hrs. The mixture was then treated with a solution of sodium borohydride in methanol at 0° C., diluted with water (20 ml) and extracted with dichloromethane. The organic extract was dried over anhydrous sodium sulfate, the solvent removed in vacuo and the crude product mixture separated by thick layer chromatography (silica gel, ethyl acetate: methanol 2:1).

The more polar product (R$_f$ 0.4, 20 mg, 25%) was the desired amide, 3',4'-dehydrovinblastine N-methylamide.

Anal. I.R.: 3680, 3440, 1725, 1680 and 1610 cm$^{-1}$.
U.V.: 302 (3.88), 292 (4.00), 285 (4.03), 264 (4.16) nm.
CD.: 262 (+6.3), 243 (−3.5), 226 (+11.2), 211 (−43.9) nm.
NMR.: 8.10 (bs, 1H, NH); 7.54 - 6.92 (m, 4H, aromatic); 6.58 (s, 1H, H-C(14)); 6.14 (s, 1H, H-C(17)); 5.86 (dd, 1H, J = 10 and 4, olefinic); 5.58 (s, 1H, HCOCOCH$_3$); 5.48 (m, 1H, olefinic); 5.34 (bd, 1H, J=10, olefinic); 3.80 (s, 3H, OCH$_3$); 3.62 (s, 3H, CO$_2$CH$_3$); 2.80 (d, 3H, J = 5, CONCH$_3$); 2.74 (s, 3H, NCH$_3$); 2.04 (s, 3H, OCOCH$_3$); 1.00 (t, 3H, J = 8, CH$_2$CH$_3$).

MS.: 188, 221, 283 (base peak), 331, 333, 345, 451, 453, 463, 467, 524, 552, 555, 610, 612, 670, 731, 733, 791.
Mol. wt.: 791.426.
Calc. for C$_{46}$H$_{57}$N$_5$O$_7$: 791.424.
C$_{46}$H$_{57}$N$_5$O$_7$·4H$_2$O. Calc. C, 64.38; H, 7.63; N, 8.16%. Found: C, 64.31; H, 7.30; N, 8.05%.

The less polar product (R$_f$ 0.75, 6 mg, 7.5%) was assigned the structure and the name, 19'-hydroxy-3',4'-dehydrovinblastine N-methylamide, on the basis of the following data:

I.R.: 3620, 3440, 1735, 1675 and 1610 cm$^{-1}$.
U.V.: 310 (3.64), 294 (3.87), 285 (3.93), 266 (4.05) nm.
CD.: 260 (+12.55), 243 (+2.8), 227 (+24.4), 210 (−40.46) nm.
NMR.: 8.12 (bs, 1H, NH); 7.68 - 7.08 (m, 4H, aromatic); 6.44 (s, 1H, H-C(14)); 6.12 (s, 1H, H-C(17)); 5.88 (dd, 1H, J = 10 and 4); 5.58 (m, 1H, olefinic); 5.52 (s, 1H, HCOCOCH$_3$); 5.32 (bd, 1H, J = 10 olefinic); 3.82 (s, 3H, OCH$_3$); 3.64 (s, 3H, CO$_2$CH$_3$); 2.82 (d, 3H, J = 5, CONCH$_3$); 2.76 (s, 3H, NCH$_3$); 2.04 (s, 3H, OCOCH$_3$); 1.03 (t, 3H, J = 8, CH$_2$CH$_3$); 0.78 (s, 3H, J = 8, CH$_2$CH$_3$).

In a related study employing a molar ratio of catharanthine: vindoline N-methylamide of 2:1, 3',4'-dehydrovinblastine N-methylamide was obtained consistently in about 50% yield.

EXAMPLE 5

Preparation of 18'-Decarbomethoxy-3',4'-dehydrovinblastine N-methylamide

In Formula I,
Z = —CH=CH—
R$_1$ = CH$_3$
R$_2$ = COCH$_3$
R$_3$ = H
R$_4$ = COOCH$_3$
R = III where R$_{11}$ = H; R$_{12}$ = CH$_2$CH$_3$ Decarbomethoxycatharanthine (134 mg, 0.5 mmol) was dissolved in dichloromethane (15 ml) and the solution cooled to −10° C. To this solution was added a solution of m-chloroperbenzoic acid (87 mg, 0.53 mmol) in dichloromethane (7.5 ml) and the whole stirred at −10° C. under a nitrogen atmosphere for 20 min. To this mixture, vindoline N-methylamide (227.5 mg, 0.5 mmol) and trifluoroacetic anhydride (410 μl, 2.5 mmol) were added and reaction mixture was stirred at −10° C. overnight under a nitrogen atmosphere. After this time, the mixture was treated with an excess (1 gm) of sodium borohydride dissolved in methanol (10 ml), diluted with water and extracted with dichloromethane. After drying over anhydrous sodium sulfate, the solvent was removed in vacuo and the residue purified by thick layer chromatography (silica gel, ethyl acetate:methanol 2:1) to provide two dimeric substances.

The least polar product (R$_f$ 0.85, 79 mg, 21.6%) was recrystallized from methanol as needles, m.p. 256-259 (dec.), and was 18'-decarbomethoxy-3', 4'-dehydrovinblastine N-methylamide.

Anal. I.R.: 3610, 3420, 1730 and 1670 cm$^{-1}$.
U.V.: 303 (3.68), 280 (3.73), 263 (3.71), 252 (3.86), 237 (4.28), 225 (4.30) nm.
CD.: 270 (+7.1), 247 (+2.4), 229 (+11.9) nm.
NMR.: 8.77 (bs, 1H, NH); 7.44-6.90 (m, 4H, aromatic); 6.78 (s, 1H, H-C(14)); 6.10 (s, 1H, H-C(17)); 5.84 (dd, 1H, J = 10 and 3, olefinic); 5.52 (s, 1H, HCOCOCH$_3$); 5.50 (d, 1H, J = 8, H-C(18')); 5.22 (d, 1H, J = 10, olefinic); 5.20 (m, 1H, olefinic); 3.90 (s, 3H, OCH$_3$); 2.80 (d, 3H, J = 5, CONCH$_3$); 2.66 (s, 3H, NCH$_3$); 2.00 (s, 3H, OCOCH$_3$); 1.0 (t, 3H, J = 8, CH$_2$CH$_3$).

MS.: 187, 281 (base peak), 286, 309, 394, 406, 453, 493, 551, 733.
Mol. wt.: 733.420. Calc. for C$_{44}$H$_{55}$N$_5$O$_5$: 733.415.
C$_{44}$H$_{55}$N$_5$O$_5$·CH$_3$OH. Calc. C, 70.56; H, 7.76; N, 9.14%.
Found: C, 69.58; H, 7.10; N, 8.83%.

The more polar product (R$_f$ 0.60, 65 mg, 18%) was obtained as an amorphous powder and 18'-epi-18'-decarbomethoxy-3',4'-dehydrovinblastine N-methylamide.

Anal. I.R.: 3440, 1730, 1675 and 1610 cm$^{-1}$.
U.V.: 300 (3.93), 293 (3.98), 287 (3.96), 256 (4.15) nm.
CD.: 262 (+6.3), 226 (−26.6) nm.

NMR.: 7.73 (bs, 1H, NH); 7.42 6.90 (m, 4H, aromatic); 6.94 (s, 1H, H-C(14)); 6.07 (s, 1H, H-C(17)), 5.84 (dd, 1H, J = 10 and 3, olefinic); 5.47 (s, 1H, HCO-COCH₃); 5.46 (m, 1H, olefinic); 5.24 (d, 1H, J = 10, olefinic); 4.56 (m, 1H, H-C(18')); 3.78 (s, 3H, OCH₃); 2.78 (d, 3H, J = 5, CONCH₃); 2.70 (s, 3H, NCH₃); 2.00 (s, 3H, OCOCH₃); 0.92 (t, 3H, J = 8, CH₂CH₃).

MS.: 187, 281, 286, 309, 365, 376, 453, 443, 551, 733.

Mol. wt.: 733.420. Calc. for $C_{44}H_{55}N_5O_5$: 733.418

$C_{44}H_{55}N_5O_5 \cdot 3H_2O$. Calc. C, 67.15; H, 7.81; N, 8.90%.

Found: C, 67.29; H, 7.30; N, 8.93%.

I claim:

1. A compound of the formula

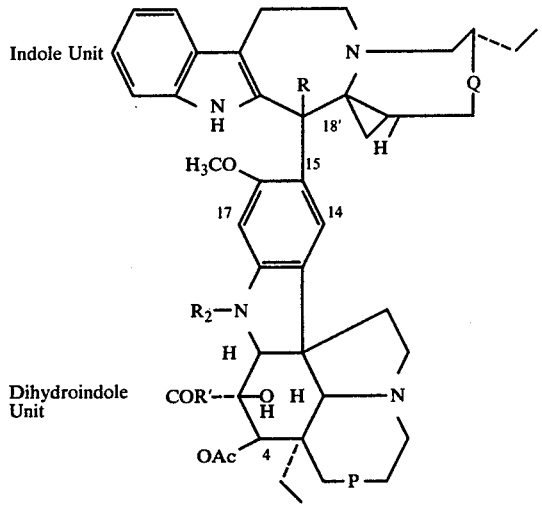

wherein Q is a single or double bond at the 3',4'-position of an indole unit, which, with a dihydroindole unit, constitutes the compound; P is a single bond; R is H or COO-alk and alk is alkyl of 1-6 carbon atoms; $R_1$ is O-alk, $NH_2$, NH-alk, $N(alk)_2$ or $NHNH_2$ and alkyl is of 1-6 carbon atoms; and $R_2$ is methyl or formyl.

2. A compound of claim 1 wherein Q is a single bond.
3. A compound of claim 1 wherein Q is a double bond.
4. A compound of claim 1 wherein $R_2$ is methyl.
5. A compound of claim 1 wherein $R_2$ is formyl.
6. 4'-Deoxovinblastine or 4'-deoxodihydrovinblastine.
7. 4'-Deoxovincristine.
8. A compound of claim 1 wherein $R_1$ is O-alk.
9. A compound of claim 1 wherein $R_1$ is $NH_2$ or NH-alk.
10. A compound of claim 1 wherein R is H.
11. A compound of claim 1 wherein R is COO-alk.

* * * * *

UNITED STATES PATENT OFFICE
CERTIFICATE OF CORRECTION

Patent No. 4,144,237　　　　　　　　　　Dated March 13, 1979

Inventor(s) James P. Kutney

It is certified that error appears in the above-identified patent and that said Letters Patent are hereby corrected as shown below:

Column 9, line 61, "$R_2 50COCH_3$" should be --$R_2 = COCH_3$--

Column 11, line 30, "$R_9 50$" should be -- $R_9 =$ --

Column 11, line 42, "$R_9 50H$" should be -- $R_9 = H$ --

Signed and Sealed this

Twenty-ninth Day of May 1979

[SEAL]

Attest:

RUTH C. MASON
Attesting Officer

DONALD W. BANNER
Commissioner of Patents and Trademarks